(12) United States Patent
Lehmann

(10) Patent No.: US 6,333,306 B1
(45) Date of Patent: Dec. 25, 2001

(54) PHARMACEUTICAL COMBINATION PREPARATIONS CONTAINING ERYTHROPOIETIN AND IRON PREPARATIONS

(75) Inventor: Paul Lehmann, Worms (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/029,859

(22) PCT Filed: Sep. 12, 1996

(86) PCT No.: PCT/EP96/03997

§ 371 Date: Mar. 16, 1998

§ 102(e) Date: Mar. 16, 1998

(87) PCT Pub. No.: WO97/09996

PCT Pub. Date: Mar. 20, 1997

(30) Foreign Application Priority Data

Sep. 14, 1995 (DE) .............................. 195 35 571

(51) Int. Cl.$^7$ ........................... A61K 38/00; A61K 35/14
(52) U.S. Cl. .................... 514/8; 514/2; 514/21; 514/814; 530/380; 530/397
(58) Field of Search ............... 514/8, 21, 814; 530/380, 397

(56) References Cited

U.S. PATENT DOCUMENTS 4,745,099 * 5/1988 Akamatsu et al. .................. 514/8
5,541,158 * 7/1996 Vance ................................. 514/8

FOREIGN PATENT DOCUMENTS 0205564  2/1991  (EP) .
0411678  8/1992  (EP) .

OTHER PUBLICATIONS

Sunder–Plassmann, G. et al. *Nephology Dialysis Transplantation* 10:2070–2076 (1995).*
Sunder–Plassmann, G. et al. *J. Am. Soc. Nephol.* 5(3):478 (1994).*
Grutzmacher et al. Effect of recombinant human erythropoietin on iron balance in maintenance hemodialysis: theoretical considerations, clinical experience and consequences. Clinical Nephrol. vol. 38, Suppl. 1, pp. S92–97, 1992.*
"Effect of recombinant human erthropoietin on iron balance in maintenance hemodialysis: theoretical considerations, clinical experience and consequences", Grützmacher et al., Clinical Nephrology, vol. 38, No. 1, 1992, pp. 92–97.
M. Wick et al. "Eisenstoffwechel, Diagnostik und Therapie der Anämien" 3. Erweiterte Auflage, Sep. 1996, Springer Verlag Wien, New York, pp. 5–14, 38–55, 65–80 und 94–98.

* cited by examiner

Primary Examiner—Karen Cochrane Carlson
Assistant Examiner—Holly Schnizer
(74) Attorney, Agent, or Firm—Arent Fox Kintner Plotkin & Kahn, PLLC

(57) ABSTRACT

The present invention is directed to a pharmaceutical combination preparation comprising 2,000–7,000 U of recombinant human erythropoietin (EPO) and 5–20 mg of an Fe(III) complex, wherein the rhEPO and the Fe(III) complex may be present in separate administration forms or in an integrated administration form.

The pharmaceutical preparation is used in the treatment of anemias or hemodialysis patients.

34 Claims, No Drawings

PHARMACEUTICAL COMBINATION PREPARATIONS CONTAINING ERYTHROPOIETIN AND IRON PREPARATIONS

The present invention relates to pharmaceutical combination preparations containing erythropoietin and iron preparations. In particular, these preparations are used in the treatment of anemia or hemodialysis patients.

The present invention is directed to a pharmaceutical combination preparation comprising 2,000–7,000 U of recombinant human erythropoietin (rhEPO) and 1–20 mg of an equivalent amount of iron ions of a physiologically tolerable iron preparation, wherein said rhEPO and said iron preparation may be present in separate administration forms or in an integrated administration form.

The use of recombinant erythropoietin in the therapy of hemodialysis patients suffering from anemia, particularly transfusion-induced anemia is well-known. Anemia in chronic diseases is the second-most frequent anemia form worldwide.

In anemias caused by a reduced erythropoiesis in the bone marrow or by disorders in the iron reutilization, the reduced regeneration of erythrocytes is the prominent feature. With a daily decline in erythrocyte regeneration around 1%, the anemia can be detected clinically only after 1–3 weeks. The daily iron requirement in normal erythropoiesis is 25 mg. Only about 1 mg thereof is from dietary sources, the manor requirement normally being met by reutilization of the hemoglobin iron after degradation of aged erythrocytes. In chronic diseases, the iron release from the reticular cells is massively reduced. The iron is held in the reticulo-endothelial system and is no longer available for erythropoiesis. Therefore, this is also referred to as "interior iron deficiency" where triggering of normal compensation mechanisms is incomplete. Reticulocytopenia and lacking hyperplasia of the erythropoiesis, which is necessary to compensate the anemia, are typical. Reduced erythropoietin secretion or activity may be an additional pathogenic factor. For example, a significant change in iron metabolism would be a compensatorily increased formation of transferrin. Thus, the basic disorder lies in the lacking release of iron from the iron depots (in the reticulo-endothelial cells) into the plasma (and thus, into the erythron as well), whereby normal compensation mechanisms are not triggered. The administration of recombinant erythropoietin is used in therapy to effect a significant increase in the number of erythrocytes.

In clinical chemistry, the serum ferritin concentration is determined for the diagnosis of anemia and disorders in iron metabolism. In case a real on deficiency is present in addition to the anemia of the chronic diseases, ferritin does not increase (in most of the cases it remains below 90–95 ng/ml). When clinical signs of infection, inflammation or a malignant disease are also present, this value indicates a combination of iron deficiency and anemia accompanied by a chronic disease. Since serum ferritin in such diseases may also react in the, sense of an acute phase protein, the diagnostic utilization of erythrocyte ferritin can be improved.

The total body iron is about 3.5 g in males and 2.5 g in females. The iron is found in the active metabolism and in storage compartments. In the active pool of a male, an average of 2100 mg is found in hemoglobin, 200 mg in myoglobin, 150 mg in tissue enzymes (hem and non-hem), and 3 mg in the iron transport compartment. In the tissue, iron is stored intracellularly as ferritin (700 mg) and hemosiderin (300 mg).

There may be a pathophysiological disorder in the bioavailability of iron, so that the iron absorption in the body is reduced. Of those approximately 10 mg being available daily by way of food, only about 1 mg is resorbed by an adult. In case of iron deficiency, the resorption increase, but rarely more than 5–6 mg unless additional iron is supplied. The precise mechanism of resorption for iron is not clear. Regulation is effected crucially by the intestinal mucosa calls. The crucial signal for the mucosa seems to be the total iron content of the body. It was demonstrated that the serum ferritin concentration is in inverse correlation to the amount of absorbed iron.

The iron is transferred to transferrin by the intestinal mucosa cells. This iron transport protein has two iron binding sites. It is synthesized in the liver. Thus, there is a mechanism by which iron is taken over by cells (e.g., intestinal mucosa, macrophages) and delivered to specific membrane receptors of erythroblasts, placenta cells or liver cells. By way of endocytosis, the transferrin/iron receptor complex enters the erythrocyte precursor cells where the iron is passed on to the mitochondria. There, hem is formed from iron and protoporphyrin.

The iron which is not needed for erythropoiesis is conveyed to two types of storage pools by transferrin. The most important depot is ferritin. This is a heterogeneous class of proteins enclosing an iron core. It is soluble and represents the active storage form in the liver (hepatocytes), bone marrow, spleen (macrophages), erythrocytes and the serum (about 100 ng/ml). The tissue ferritin pool is highly labile and quickly available in case iron is required. The circulating serum ferritin comes from the reticulo-endothelial system, and its circulating concentration goes parallel to that of total body iron (each ng/ml corresponding to 8 mg of iron reserve).

In the case of hemodialysis patients, the iron requirement of patients treated with rhEPO was found to be quite considerable. As a rule, an additional iron therapy was conducted with these patients because the EPO can develop its optimum effect only in case the corresponding iron depots in the body are filled as much as possible. To date, it has been common to administer high doses of iron preparations in order to fill the iron depots as much as possible, However, excessive doses of iron preparations may also give rise to undesirable side effects in patients. In particular, the intravenous application of iron preparations is not safe in physiological terms due to the extreme toxicity of iron ions. In patients where the situation of allergic reactions is well-known, e.g., asthmatics, the use of certain iron preparations is even discouraged, as a rule. Estimating the filling level of the iron depots is possible by determining the ferritin protein and by determining the transferrin saturation (M. Wick, W. Pingerra, P. Lehmann, "Eisenstoffwechsel, Diagnose und Therapie der Anämien", pp. 5–14, 38–55, 65–80, 94–98, third advanced edition, September 1996, Springer Verlag, Vienna, N.Y.), wherein said transferrin saturation represents the iron flow from the depots to the marrow, while the serum ferritin value is a measure of stored iron.

The iron depots are regarded as "filled" when the serum ferritin is >150 μg/l and a transferrin saturation of >20% is present. P. Grützmacher et al., in Clinical Nephrology, Vol. 38, No. 1, 1992, pp. 92–97, describe that maximum response to the EPO therapy can be assumed under these conditions.

At present, one speaks of a "correction phase" and a "maintenance phase" in the iron therapy of EPO-treated dialysis patients. During the correction phase, iron preparations are administered at dosages as high as possible in order to refill the iron depots as rapidly as possible. Conveniently, the application of suitable iron preparations is then effected by way of intravenous bolus injection. The iron depots are then "maintained filled" during the maintenance phase using lower iron dosages. The application of suitable iron preparations in this phase is not effected as a rapid bolus injection but in the form of common infusion preparations or by oral administration.

The iron requirement of rhEPO-treated hemodialysis patients may be quite considerable in both the correction and maintenance phases. In order to synthesize 1 g/dl hemoglobin during the correction phase, 150 mg of iron is required which either is delivered from endogenic iron depots or must be supplied exogenously. Similarly, there is an increased iron requirement during the maintenance phase because each treatment of hemodialysis patients gives rise to a minor loss of blood. Over a one year period the loss of iron is estimated to be about 1000 mg of iron (3 mg/day) On the long run, such loss can only be balanced via the exogenic route. In principle, oral and intravenous administration forms are available for this purpose.

As the oral iron resorption is only about 1 mg/day and less than 3 mg/day under extreme strain (with oral administration of about 300 mg of Fe(III)/day), intravenous application of larger amounts of iron is increasingly preferred. Currently, two iron preparations applicable by the intravenous route are available on the German pharmaceutical market. These are the "ferrlecit" and "ferrum vitis" drugs. Ferrlecit is an iron(III) gluconate complex, while "ferrum vitis" is an iron(ITI) hydroxide saccharate complex.

Indeed, the various problems of a high dosage, long-term oral iron therapy can be avoided with relative ease by using the intravenous, subcutaneous application of iron(III) during hemodialysis treatment, because there is a safe intravenous, subcutaneous access, and injections can be effected without further strain for the patient. In recent years, this procedure has. found more widespread use based on the assumption that administration forms with relatively few side effects were available with the "ferrlecit" and "ferrum vitis" preparations. Meanwhile, however, some side effects were pointed out in association with ferrlecit therapy in autologous blood transfusion, and the indication range for parenteral ferrlecit therapy was restricted significantly. Attention has been drawn to possible circulatory reactions ranging as far as collapsing and to possibly occurring anaphylactic reactions. Furthermore, the maximum allowed daily dose has been determined to be 2 ampoules of 5 ml, corresponding to 125 mg of iron.

Thus, the intravenous administration of either iron preparation is not trivial, because side effects must be expected in the application of either drug, all the more so when larger amounts have to be injected relatively quickly. Furthermore, the intravenous administration of iron preparations may cause problems as far as acute phase reactions if the iron dose is too high or is administered without optimum balance to the EPO dose.

Obviously, the high iron dosages which have to be administered to EPO-treated dialysis patients are disadvantageous. The risk of cardiac infarction is increased and also, the risk of developing iron cirrhosis is significantly increased. Within the scope of dialysis patient treatment, an adequate supply of iron as well as a suitable method for determining iron deficiency has considerable therapeutic benefit because insufficient iron availability is one of the major reasons for insufficient effectiveness of EPO and EPO resistance, respectively.

Excessively high dosages of iron-containing preparations may also give rise to iron intoxications. Elemental iron has a toxic effect on the gastrointestinal tract, the cardiovascular and the central nervous system. The oral lethal dose of elemental iron ranges between 200 and 250 mg/kg. The most frequently used iron tablets are ferrous sulfate (containing about 20% of elemental iron), ferrous fumarate (containing about 30% of elemental iron) or ferrous gluconate (containing about 10% of elemental iron).

There are four typical phases of iron intoxication. Phase I (within the first 6 hours after intoxication): vomiting, diarrhoea, hyperexcitability, stomach ache, attacks, apathy and coma may occur, Irritations of the gastrointestinal mucosa may give rise to hemorrhagic gastritis. Tachypnoea, tachycardia, hypotension, shock, coma and metabolic acidosis may occur at high serum levels. Phase II (within the first 10–14 hours after intoxication): within a latency period which may last up to 24 hours, there is an apparent improvement. Phase IIT (12–48 hours after intoxication): shock, hypoperfusion and hypoglycemia occur. The serum iron levels may be normal. Liver damage with elevated GPT, fever, leukocytosis, disturbed coagulation, T inversion in the ECG, disturbed orientation, restlessness, apathy, attack tendency, coma, shock, acidosis, and death may occur. Phase TV (2–5 weeks later): possible complications due to a pylorus, antrum or other intestinal obstructions, liver cirrhosis or damage of the central nervous system may become prominent.

It was the object of the invention to provide a combination preparation of recombinant human erythropoietin and an iron preparation containing an amount of EPO and iron ions which is optimally adjusted for the therapy of iron metabolism disorders. In particular, the demonstrated risks and especially the acute phase reactions are to be avoided by means of said combination preparations. In patients being treated with rhEPO; optimum EPO effect is to be achieved and EPO resistance avoided.

The combination preparation of the invention comprises 2,000–7,000 U of rhEPO and 1–20 mg of an equivalent amount of iron ions of a physiologically tolerable iron preparation, particularly an Fe(II) or Fe(III) complex, wherein the rhEPO and the iron preparation are present as combination preparations.

In the meaning of the present invention, the term "combination preparations" should be understood as referring not only to those drug packs wherein the EPO and the iron preparation are present formulated together in a ready-for-sale packing unit (so-called combination pack), but also to those drug packs which either contain a suitable amount of EPO or a suitable amount of an iron preparation in the form of a single preparation, the single preparations being formulated with respect to the amount of ingredients in such a way that it is possible in the meaning of the invention to effect combined administration with the respective other preparation. In these cases, the pharmaceutical manufacturers or the drug importers normally include a package circular prescribed by law in many countries, which includes instructions or information on the combined administration of the single preparations. Preferably, the combination preparations may be present in an integrated administration form wherein the respective amounts of EPO and the iron preparation are present together in one container.

In the meaning of the invention, oral or parenteral administration forms are possible as iron preparations. In principle, these may be single preparations containing a physiologically tolerable iron salt or an iron complex compound as active substance, or combination preparations as well which, in addition to the physiologically tolerable iron preparation, contain further active substances such as vitamins, folic acid, thiamine chloride, riboflavin, pyridoxine, ascorbic acid, nicotinamide, calcium pantothenate, etc.

For example, physiologically tolerable iron salts or iron complex compounds are iron(II) sulfate, iron(II) fumarate, iron(III) citrate, iron(II) gluconate, iron(II) succinate, iron (II) chloride, iron(II) glycine sulfate complex, iron(II) aspartate, sodium iron(III) gluconate complex, iron(III) hydroxide polymaltose complex, or ferric sorbitol citrate complex. In particular, preferred iron preparations are Fe(III) complexes, especially those having a molecular weight of between 30,000 and 100,000 D. Particularly preferred is Fe(III) saccharate. Here, the commercially available "ferrum vitis" preparation (Neopharma Co., Germany) may be used. As a result of the low iron dosage according to the invention, labile iron complexes such as iron gluconate (m.w. about 1000 D; ferrlecit) may also be used in the combination preparation, although such labile iron complexes liberate relatively large amounts of ionized iron which would give rise to toxicity when quite large quantities are applied intravenously.

When referring to the amount of iron preparation hereinafter, this is basically understood to be the equivalent amount of iron ions, i.e., Fe(II) or Fe(III) ions to be applied. By way of this standardization, the amount of any iron preparation can be calculated on the basis of its known molecular weight. In the case of iron(III) gluconate ×2 $H_2O$, for example, the amount of iron is 80.5 mg when administering a 695 mg amount of iron preparation. When administering 280 mg of anhydrous iron(II) succinate, for example, the amount of iron is 95.2 mg.

Instead of the rhEPO protein (cf., European patent specification EP 0,205,564; EP 0,411,678), modifications of said protein having a higher or lower molecular weight than 34,000 Da (molecular weight of urinary EPO), isoforms of the enzyme or proteins with different glycosylation may also be used. Moreover, in principle, those proteins derived from the amino acid sequence of natural EPO with a length of 166 amino acids by way of deletions, substitutions or extensions are also possible. Essentially, such proteins have physiological properties comparable to rhEPO. In particular, such proteins have biological properties inducing the bone marrow to increase the production of reticulocytes and red blood cells and/or to increase hemoglobin synthesis or iron absorption. Instead of these proteins, low molecular weight substances may also be used, which are referred to as EPO mimetics and bind to the same biological receptor. Preferably, these mimetics may also be administered by the oral route. The amount of such proteins or mimetics to be administered is determined by comparing the biological activities of EPO and said active substances.

For the treatment of hemodialysis patients, the combination preparation according to the invention contains especially 3,000 to 7,000 U of rhEPO, particularly 4,000 to 6,000 U of rhEPO, and preferably about 5,000 U of rhEPO. Particularly, the amount of iron ions is 3–20 mg, preferably 5–20 mg, with 10 mg being particularly preferred. For the treatment of anemia patients, the optimum dose is 2,000 to 4,000 U of rhEPO, preferably about 3,000 U. In this case, the amount of iron ions is 3–15 mg, particularly about 5 mg.

In their combination, the rhEPO and iron complex concentrations according to the invention permit optimum adjustment and treatment of hemodialysis or anemia patients and do not give rise to acute phase reactions in intravenous iron therapy.

Treatment using the combination preparation is effected once to five times, preferably up to four times a week, wherein the total amount per patient should not exceed 60 mg of iron ions per week in the case of hemodialysis patients treatment. When treating anemia, the total amount should not exceed 20 mg of iron ions per week. In clinical practice, the combination preparation according to the invention is particularly advantageous in that it may be used in both the correction and maintenance phases of the iron therapy of hemodialysis patients without causing toxicity. To date, different amounts of iron have been administered, where initially, lower dosages of iron ions have been administered in the correction phase as compared to the maintenance phase. Surprisingly, such different dosage is no longer required when using the combination preparations according to the invention. The amounts of EPO and iron preparation are mutually adjusted in such optimal fashion that differentiation between maintenance dose and correction dose is not required. In this way, increased safety in the treatment of hemodialysis or anemia patients is achieved because there is no more chance of confusing the optimum dosage of iron preparation.

When applying the combination preparations, rhEPO and iron complex may be administered in a so-called fixed combination, i.e., in a single pharmaceutical formulation containing both compounds. For example, this may be an injection solution or an infusion solution or a lyophilizate thereof filled in ampoules, for example. Such administration form is advantageous in that the EPO is stabilized by the iron complex during production and storage of the administration form. In the case of a lyophilizate, the EPO will be activated by the iron complex after dissolving the lyophilizate. The fixed combination of both active substances in the form of a lyophilizate has the further advantage of easy and safe handling. The lyophilizate is dissolved in the ampoule by adding pharmaceutically common injection vehicles and is administered intravenously.

EPO and iron complex may also be provided in the form of separate pharmaceutical formulations. As a rule, this is effected using a single packing unit comprising two containers, the first being a suitable EPO administration form (lyophilizate, injection or infusion solution), and the second representing a suitable administration form for the iron preparation. The free combination which may be provided in a single packing unit (drug pack) is advantageous in that each patient to be treated can individually be given a quantity of EPO and iron preparation, which can be assigned directly. In addition, such combination preparations offer the advantage of more safety for therapeutical success because each of the optimally adjusted amounts of single preparations has been determined, and confusion with other commercially available single preparations offered with various dosages is excluded to a great extent. Moreover, it must be contemplated that drug preparations having different dosages are frequently traded in various countries due to the national requirements and thus, there is a higher risk of confusing the various quantity ratios of the individual active substances (EPO and iron complex). Furthermore, the combination preparations according to the invention minimize the risk of an erroneously excessive iron medication which possibly might occur if conventional iron preparations from separate drug packs are used together with the EPO administration. The combination preparations of the invention ensure safe therapy and easy handling by the personnel in charge or within the scope of self-medication carried out by the patient. In the present case, it is also possible, for example, to provide one active substance as an injection solution and the other active substance (iron complex) as an administration form for oral administration.

In case the EPO active substance is provided as a lyophilizate, the drug packs (combination packs) contain the appropriate quantity of EPO in glass ampoules or capsules. The iron preparation may be present in solid form (tablet, powder, granulate, lyophilizate, etc.) or in liquid form in a separate container. Furthermore, the combination pack preferably includes a reconstituting solution in order to dissolve the lyophilizate of the active substance either alone or together with the solid iron preparation. In case the iron preparation is present as a ready-for-use solution, the solution may be mixed together with the EPO solution if EPO and iron preparation are to be applied together, In principle, the iron preparation may also be provided as a concentrate to be added to conventional infusion solutions, permitting slower application over several hours. In this event, a small volume of solution containing the iron complex (about 0.5–10 ml) is added to the ready-for-use injection solution of about 500–1000 ml.

In the meaning of the invention, another possibility is providing each of the single preparations of EPO and iron preparations as an independent drug, the single preparations being formulated in such a way as to contain the required quantities of individual substances for the EPO and iron complex combination according to the invention. As a rule, the drug packs include the prescribed package circulars wherein appropriate directions for the combined administration of EPO and/or iron preparations in the required amounts are included. Appropriate directions may also be included as package printing on the drug pack (secondary packing means) or on the primary packing means (ampoule, blister strip, etc.). Thus, in the case of the EPO-containing drug having 2,000–7,000 units of EPO, for example, there are directions that this preparation should be administered especially together with an iron complex containing 1–20 mg of iron. Vice versa, there are directions for the combined administration with 2,000–7,000 U of EPO in the case of iron preparations.

The pharmaceutical administration forms are produced according to conventional procedures well-known in galenic technology using common pharmaceutical adjuvants.

When conducting the combination therapy using the combination preparation according to the invention, the maximum weekly dosage can be concluded in a quite simple fashion by determining the diagnostic parameters for the iron status, particularly the iron, transferrin, transferrin saturation and ferritin parameters. Adjustment of the patient during the correction and maintenance phases was found to be optimal when

| ferritin is | 100–300 $\mu$g/l (corresponding to depot iron(III) of 800–1200 mg), and the |
|---|---|
| transferrin saturation is | 20–40%. |

Preferably, the ferritin concentration is at least 125 $\mu$g/l, particularly at least 150 $\mu$g/l, and up to 270 $\mu$g/l at maximum, especially up to 250 $\mu$g/l at maximum. Advantageously, the iron concentration is between 10–20 $\mu$mol/l (corresponding to about 56–112 $\mu$g/dl) and the transferrin concentration between 30–60 $\mu$mol/l (corresponding to about 240–480 mg/dl). The transferrin saturation is defined as the ratio of serum/plasma iron concentration to serum/plasma transferrin concentration (multiplied by a correction factor of 1.41). It is a non-dimensional figure not depending on the patient's hydration condition. The transferrin saturation is calculated according to the formula:

transferrin saturation (%)=(iron[$\mu$g/dl]×100)/(transferrin[mg/dl]×1.41)

Optimum adjustment of the patient is achieved when the ratio of transferrin saturation (in %) to ferritin concentration (in $\mu$g/l) ranges from 5–40% This parameter is defined as transferrin/ferritin saturation (TfF saturation). It is calculated according to the formula:

TfF saturation=(transferrin saturation ln%)×100/(ferritin[$\mu$g/l])

The value for this parameter is preferably in the range of 10–40, particularly at 15–25 [%×l/$\mu$g].

For example, when administering from 1 to 6 ampoules, preferably up to 4 or 5 ampoules per week (one ampoule containing 2,000–7,000 U of rhEPO and 1–20 mg of iron complex), the optimum adjustment of the patient is examined by diagnosis using these parameters.

In order to safely exclude undesirable side effects, the acute phase parameter CRP (5 mg/l±100%) [CRP=C reactive protein) is measured, with CRP currently being regarded as the best protein marker of inflammatory reactions. In addition, the liver parameters GPT (glutamate pyruvate transaminase), GOT (glutamate oxalic acetate transaminase) and $\gamma$-GT ($\gamma$-glutamyltransferase) may be determined, which should fall within the following ranges: (determination at 37° C.): GPT: <50 U/l; GOT: <50 U/l; $\gamma$-GT: <40 U/l, with the GPT parameter currently ranking first in liver diagnostics.

Furthermore, the hematological control parameters such as hematocrit (fraction of red blood cells in total volume) or the increase in hypochromic erythrocytes may optionally be utilized. In case the control parameters show higher increase, the weekly iron dose must be reduced, and rhEPO should be administered in addition. In case the control parameters, particularly the transferrin saturation, show lower values, the weekly iron administration must be increased.

Surprisingly, it has also been found in the meaning of the invention that the predetermination of a patient-individual, optimum therapeutical dose of EPO and iron ions for the treatment of anemia may also be effected by determining the soluble TfR (transferrin receptor). The optimum therapeutical dose of EPO and iron(III) is reached when the concentration of the soluble TfR does not increase anymore. To ensure that sufficient mobilizable iron is present, the i.v. iron dose and the EPO administration are increased alternately until a plateau is reached. This corresponds to a concentration of 1,500–2,000 $\mu$g/l TfR.

When conducting the combination therapy using the combination preparation of the invention to treat anemia, the weekly maximum dosage can be concluded in a quite simple fashion by determining the diagnostic parameters transferrin receptor (TfR), ferritin and the ratio of TfR to ferritin. It was found that the patient is optimally adjusted in the correction and maintenance phases when

| ferritin is | 100–300 $\mu$g/l (corresponding to depot iron(III) of 400–1200 mg), |
|---|---|
| TfR/ferritin is | >15 |

Advantageously, the TfR concentration is between 1500–2500 $\mu$g/l. The concentration ratio of TfR (in $\mu$g/l) to ferritin (in $\mu$g/l) is particularly in the range of 15–35, preferably at values above 20.

For example, when administering from 1 to 6 ampoules, preferably up to 4 or 5 ampoules per week (one ampoule containing 3,000 U of rhEPO and 5 mg of iron complex), the optimum adjustment of the patient is examined by diagnosis using these parameters. In this event, these are not hemodialysis patients, in particular, but patients undergoing therapy with EPO and/or iron preparations due to an anemia of other origin.

In order to safely exclude undesirable side effects, the acute phase parameter CRP (2–10 mg/l) [CRP=C-reactive protein) is measured. In addition, the liver parameter GPT (glutamate pyruvate transaminase) may be determined, which should be <50 U/l at 37° C. (<30 U/l at 25° C.). Furthermore, the hematological control parameters such as hematocrit (fraction of red blood cells in total volume) or the increase in hypochromic erythrocytes may optionally be utilized, wherein the reticulocytes may increase to a value of up to 15/1000–30/1000. The typical hemoglobin concentration is about 12–18 g/dl. In case the soluble TfR shows higher increase, the weekly iron dose must be increased as high as up to 35 mg. If the soluble TfR shows lower values, the weekly EPO dose must be increased.

The determination of the iron status is effected by analyzing samples of body fluids (blood, serum, urine, etc.) from the patients in question. For the determination of the iron status, particularly the concentrations of iron, transferrin, ferritin, transferrin receptor, the transferrin saturation, and the transferrin/ferritin saturation are determined. With hemodialysis patients, the iron, transferrin, ferritin and transferrin saturation parameters are preferably determined according to per se common analytical methods. In particular, the determination of the transferrin/ferritin. saturation value is relevant. In the case of anemia patients whose anemia has not been caused by hemodialysis, the ferritin concentration and the concentration of transferrin receptor are determined above all. In particular, the determination of the ratio of transferrin receptor to ferritin (transferrin receptor/ferritin saturation value) is relevant.

An optimum combination preparation for the treatment of anemia patients, which is in accordance with the invention in this meaning, comprises 2,000–4,000 U of EPO and 3–10 mg, preferably 5 mg of iron ions, preferably of an Fe(III) complex, where the EPO and the Fe(III) complex may be present in separate administration forms or in an integrated administration form.

The administration forms according to the invention also permit application of the iron preparations 1 to 3 days prior to EPO application in order to fill the iron depots already before the EPO treatment Furthermore, the invention is directed to the use of 3,000–7,000 U of rhEPO and 5–20 mg of iron ions of a physiologically tolerable iron preparation in the production of combination preparations for the treatment of hemodialysis patients.

To examine the iron metabolism, the concentration of iron in the blood and the iron binding capacity are determined in clinical chemistry. Both of the tests should always be carried out because the mutual relationship of these measuring results is important. Usually, the normal serum iron levels in males are between 75 and 150 mg/dl and between 60 and 140 mg/dl in females. The total iron binding capacity is between 250 and 450 mg/dl. The serum iron level varies over the day. It is decreased in case of iron deficiency and anemias in the course of chronic diseases. It is increased in case of hemolysis and syndromes involving iron overloading (e.g., herochromatosis or hemosiderosis). Patients undergoing oral iron medication may have normal iron serum levels, although they actually have iron deficiency The total iron binding capacity (=transferrinx2) is increased in case of iron deficiency, whereas it is decreased in case of anemias in the course of chronic diseases.

In addition, the serum ferritin level is determined. Ferritin is an iron-storing glycoprotein of which tissue-typical isoferritina are existing and which can be determined in the serum by immunological means, e.g., by a radioimmunoassay (RIA) or by turbidimetric methods as well. The ferritin value is a measure for iron storage in the tissue. In most of the laboratories, the normal range is between 30 and 300 ng/ml, and the geometrical mean value is 88 in males and 49 in females. The serum ferritin values are in close relationship to the total iron reserve of the body. Therefore, decreased ser,m ferritin levels are found only in case of iron deficiency. Increased levels are found in case of iron overloading. Likewise, increased serum ferritin levels are found in case of liver lesions or in association with some types of neoplasia, where ferritins may be bound to acute phase proteins. Similarly, the serum transferrin receptor may be determined using an enzyme-enhanced immune absorption test (enzyme-linked immunosorbent assay=ELISA), wherein a monoclonal antibody against the soluble receptor is used. The reference range is between 0.5–3 mg/l. The level is increased in case of slight deficiency in the iron depots. The concentrations of specific erythrocyte ferritins may be determined in order to characterize the iron depots, particularly it the serum ferritin cannot be utilized in case of tissue lesions or due to acute phase react ions.

For the examination of the iron metabolism, the erythrocyte ferritin level is determined in addition. In heparinized blood, the erythrocytes are separated from the leukocytes and thrombocytes (which also contain ferritin), using centrifugation. This is followed by lysis of the erythrocytes and immunological determination of the stored ferritin. The erythrocyte ferritin mirrors the status of the iron depots during the last 3 months (i.e., during the lifetime of an erythrocyte). The normal values are generally between 5 and 48 attograms (ag) per erythrocyte. Values of <5 are found in iron deficiency anemias, increased values (frequently >100) in case of iron overloading (e.g., hemochromatosis). The determination of zinc protoporphyrin is of similar significance.

The invention will be illustrated in more detail with reference to the following examples, wherein the indicated amounts in case of the iron preparations refer to the equivalent amount of iron ions (rather than the amount of administered iron complex).

EXAMPLE 1

Patient A (Hemodialysis)

a) Standard Preparation

According to the conventional therapy procedure, the patient was administered 100 mg of iron(III) complex once per week and 5,000 U of rhEPO i.v. three times per week. Here, the transferrin, transferrin saturation, CRP, GOT/GPT, and γ-GT diagnostic parameters were within the normal ranges; the ferritin value was found to be too high, being 800–1300 μg/l. In order to decrease the ferritin value to <500 μg/l, 5000 U of rhEPO was administered three times a week over a period of 3 weeks.

b) Preparation of the Invention

When the combination preparation according to the invention, consisting or 10 mg of iron(III) saccharate and 5,000 U of ream was subsequently administered three times per week, a ferritin value in the normal range was obtained and was maintained in further treatment. All the other parameters were in the normal ranges as well.

EXAMPLE 2
Female Patient B (Hemodialysis)
a) Standard Preparation

According to Example 1, the female patient B received 50 mg of iron(III) preparation once per week and 5.000 U of rhEPO three times per week. Despite the lower iron dose as in Example 1, the ferritin and transferrin saturation parameters were too high.

The ferritin value was decreased to <500 µg/l and the transferrin saturation to <25% by administering 5,000 U of rhEPO three times a week over a period of 3 weeks.

b) Preparation of the Invention

After administering the combination preparation according to the invention of 10 mg of iron(III) preparation and 5,000 U of rhEPO twice to three times a week, all the values were within a reasonable range, and even upon further treatment with the preparation of the invention, extreme values occurred no more.

EXAMPLE 3
Patient C (Hemodialysis)
a) Standard Preparation

Patient C received 50 mg of the iron(III) preparation twice a week and 2000 U of rhEPO twice a week. In this case, it was found that the ferritin value being 1500–2500 µg/l is very high and the γ-GT is increasing. By omitting the iron infusions, the ferritin values were lowered to 500 µg/l within 3 weeks.

b) Preparation of the Invention

Again, by subsequent administration of the combination preparation according to the invention of 10 mg of iron(III) gluconate and 5,000 U of rhEPO for three times, the normal values of ferritin, transferrin saturation, CRP, GOT, and γ-GT were obtained and maintained in further treatment.

EXAMPLE 4
Patient D (Anemia Patient)
a) Standard Preparation

According to the conventional therapy procedure, the patient was administered 100 mg of iron(III) complex once per week and 5,000 U of rhEPO i.v. three times per week. Here, the transferrin, transferrin saturation, CRP, GOT/GPT, and γ-GT diagnostic parameters were within the normal ranges; the ferritin value was found to be too high, being 800–1300 µg/l; the value for the transferrin receptor was between 100–500 µg/l and thus, too low.

To increase the transferrin receptor value to values above 1500 µg/l and to decrease the ferritin value to values below 500 µg/l, 5,000 U of rhEPO was administered three times a week over a period of 3 weeks.

b) Preparation of the Invention

When the combination preparation according to the invention, consisting of 5 mg of iron(III) saccharate and 3,000 U of rhEPO was subsequently administered five times per week, a transferrin receptor value and ferritin value in the normal range was obtained and maintained in further treatment. All the other parameters were in the normal ranges as well.

EXAMPLE 5
Patient E (Anemia Patient)
a) Standard Preparation

According to Example 4, patient E received 50 mg of iron (III) preparation once per week and 5,000 U of rhEPO three times per week. Despite the lower iron dose as in Example 4, the ferritin and transferrin saturation parameters were too high.

The transferrin receptor value was increased to values above 1500 µg/l, and the ferritin value was decreased to <500 µg/l and the transferrin saturation to <25% by administering 5,000 U of rhEPO three times a week over a period of 3 weeks.

b) Preparation Of the Invention

After administering the combination preparation according to the invention of 5 mg of the iron(III) preparation and 3,000 U of rbEPO four to five times a week, all the values were within a reasonable range, and even upon further treatment with the preparation of the invention, extreme values occurred no more.

EXAMPLE 6
Patient F (Anemia Patient)
a) Standard Preparation

Patient F received 50 mg of the iron(III) preparation twice a week aid 2,000 U of rhEPO twice a week. In this case, it was found that the transferrin receptor value is very low, being 100–800 µg/l, and the ferritin value, being 1500–2500 µg/l, is very high, and the γ-GT is increasing. By omitting the iron infusions, the transferrin receptor values were increased to values above 1500 µg/l, and the ferritin values were lowered to <500 µg/l within 3 weeks.

b) Preparation of the Invention

Again, by subsequent administration of the combination preparation according to the invention of 5 mg of iron(III) gluconate and 3,000 U of rhEPO for five times, the normal values of ferritin, transferrin receptor, transferrin saturation, CRP, GOT, and γ-GT were obtained and maintained in further treatment.

What is claimed is:

1. A method for the treatment of hemodialysis patients or patients exhibiting anemia, comprising administering to a patient in need of such treatment effective amounts of erythropoietin and a physiologically tolerable iron preparation contained in a pharmaceutical combination preparation, wherein the pharmaceutical combination preparation contains about 2,000–7,000 U of erythropoietin and a quantity of iron preparation equivalent to about 1–20 mg of iron ions, wherein the erythropoietin and the iron preparation are administered both in the correction phase and the maintenance phase of iron therapy, wherein the iron doses are, independently, 1–20 mg/week in the correction phase and the maintenance phase and wherein the erythropoietin doses are, independently, up to 15,000 U/week in the correction phase and the maintenance phase.

2. The method of claim 1, wherein the pharmaceutical combination preparation contains about 3,000–7,000 U of erythropoietin and a quantity of iron preparation equivalent to about 5–20 mg of iron ions.

3. The method of claim 1, wherein the pharmaceutical combination preparation contains 5,000 U of erythropoietin and a quantity of iron preparation equivalent to 10 mg of iron ions.

4. The method of claim 1, wherein the pharmaceutical combination preparation contains about 2,000–4,000 U of erythropoietin and a quantity of iron preparation equivalent to about 3–10 mg of iron ions.

5. The method of claim 4, wherein the pharmaceutical combination preparation contains 3,000 U of erythropoietin and a quantity of iron preparation equivalent to 5 mg of iron ions.

6. The method of claim 1, wherein the iron preparation comprises a complex having a molecular weight of about 30,000–100,000 daltons.

7. The method of claim 6, wherein the complex comprises Fe(III) saccharate.

8. The method of claim 1, wherein the iron preparation comprises Fe(III) gluconate.

9. The method of claim 1, wherein the treatment is the treatment of hemodialysis patients.

10. The method of claim 1, wherein the treatment is the treatment of patients exhibiting anemia.

11. The method of claim 1, wherein the amounts of erythropoietin and iron preparation administered are adjusted during said treatment to produce a ferritin concentration in a body fluid sample from the patient of about 100–300 μg/l.

12. The method of claim 1, wherein the amounts of erythropoietin and iron preparation administered are adjusted during said treatment to produce an iron concentration in a body fluid sample from the patient of about 10–20 μmol/l.

13. The method of claim 1, wherein the amounts of erythropoietin and iron preparation administered are adjusted during said treatment to produce a transferrin concentration in a body fluid sample from the patient of about 240–480 mg/dl.

14. The method of claim 1, wherein the amounts of erythropoietin and iron preparation administered are adjusted during said treatment to produce a transferrin saturation in a body fluid sample from the patient of about 20–40%.

15. The method of claim 1, wherein the amounts of erythropoietin and iron preparation administered are adjusted during said treatment to produce a transferrin/ferritin saturation in a body fluid sample from the patient of about 5–40%×l/μg.

16. The method of claim 1 for the treatment of patients exhibiting anemia, wherein the amounts of erythropoietin and iron preparation administered are adjusted during said treatment to produce a ferritin concentration in a body fluid sample from the patient of about 100–300 μg/l.

17. The method of claim 1 for the treatment of patients exhibiting anemia, wherein the amounts of erythropoietin and iron preparation administered are adjusted during said treatment to produce a transferrin receptor concentration in a body fluid sample from the patient of about 1500–2500 μg/l.

18. The method of claim 1 for the treatment of patients exhibiting anemia, wherein the amounts of erythropoietin and iron preparation administered are adjusted during said treatment to produce a ratio of the transferrin receptor concentration to the ferritin concentration in a body fluid sample from the patient of greater than about 15.

19. A method for the treatment of hemodialysis patients exhibiting anemia, comprising
(a) monitoring at least one parameter selected from the group consisting of ferritin concentration, iron concentration, transferrin concentration, transferrin saturation and transferrin/ferritin saturation in a body fluid sample from the patient to determine the at least one parameter with respect to a target range of about 100–300 μg/l for the ferritin concentration, about 10–20 μmol/l for the iron concentration, about 240–480 mg/dl for the transferrin concentration, about 20–40% for the transferrin saturation or about 5–40%×l/μg for the transferrin/ferritin saturation;
(b) if the at least one parameter is determined to be less than the lower limit of the target range, administering erythropoietin and a physiologically tolerable iron preparation contained in a pharmaceutical combination preparation, which combination preparation contains about 2,000–7,000 U of erythropoietin and a quantity of iron preparation equivalent to about 1–20 mg of iron ions, to the patient in amounts sufficient to bring the at least one parameter within the target range; and thereafter
(c) conducting maintenance treatments by administering the erythropoietin and iron preparation to the patient in amounts sufficient to keep the at least one parameter within the target range;
wherein the erythropoietin and the iron preparation are administered both in the correction phase and the maintenance phase of iron therapy, wherein the iron doses are, independently, 1–20 mg/week in the correction phase and the maintenance phase and wherein the erythropoietin doses are, independently, up to 15,000 U/week in the correction phase and the maintenance phase.

20. The method of claim 19 wherein
(i) in step (b), the erythropoietin and iron preparation administration is repeated at the same or different amounts thereof until the at least one parameter is determined to be within the target range;
(ii) in step (b), the amounts of the erythropoeitin and iron preparation used in the first administration successful in bringing the at least one parameter within the target range are optimal amounts; and thereafter
(iii) said optimal amounts are the amounts of the erythropoeitin and iron preparation used in the maintenance treatments of step (c).

21. The method of claim 19 wherein
(i) in step (b), if the at least one parameter is determined to be less than the lower limit of the target range, conducting an initial treatment by administering erythropoeitin and a physiologically tolerable iron preparation in amounts believed to be sufficient to bring the at least one parameter within the target range;
(ii) after the first administration in step (i), if the at least one parameter is determined to be less than the lower limit of the target range, conducting an treatment by administering the erythropoeitin and iron preparation in amounts believed to be sufficient to bring the at least one parameter within the target range;
(iii) repeating step (ii) until the at least one parameter is determined to be within the target range and, once the at least one parameter reaches the target range, the amounts of erythropoeitin and iron preparation used in the most recent repeat of step (ii) are considered optimal amounts; and thereafter
(iv) conducting maintenance treatments in step (c) by administering the erythropoeitin and iron preparation at the optimal amounts.

22. A method for the treatment of patients exhibiting anemia, comprising
(a) monitoring at least one parameter selected from the group consisting of ferritin concentration, transferrin receptor concentration, and the ratio of transferrin receptor concentration to ferritin concentration in a body fluid sample from the patient to determine the at least one parameter with respect to a target range of about 100–300 μg/l for the ferritin concentration, about 1500–2500 μg/l for the transferrin receptor concentration or greater than about 15 for the ratio of transferrin receptor concentration to ferritin concentration;
(b) if the at least one parameter id determined to be less than the lower limit of the target range, administering erythropoietin and a physiologically tolerable iron preparation contained in a pharmaceutical combination preparation, which combination preparation contains about 2,000–7,000 U of erythropoietin and a quantity of iron preparation equivalent to about 1–20 mg or iron ions; in amounts sufficient to bring the at least one parameter within the target range; and thereafter (c) conducting maintenance treatments by administering the erythropoietin and iron preparation to the patient in amounts sufficient to keep the at least one parameter within the target range;

wherein the erythropoietin and the iron preparation and administering both in the correction phase and the maintenance phase of iron therapy, wherein the iron doses are, independently, 1–20 mg/week in the correction phase and the maintenance phase and wherein the erythropoietin doses are, independantly, up to 15,000 U/week in the correction phase and the maintenance phase.

23. The method of claim 22 wherein (i) in step (b), the erythropoietin and iron preparation administration is repeated at the same or different amounts thereof until the at least one parameter is determined to be within the target range;

(ii) in step (b), the amounts of the erythropoietin and iron preparation used in the first administration successful in bringing the at least one parameter within the target range are optimal amounts; and thereafter (iii) said optimal amounts are the amounts of the erythropoietin and iron preparation used in the maintenance treatments of step (c).

24. The method of claim 22 wherein (i) in step (b), if the at least one parameter is determined to be less than the lower limit of the target range, conducting an initial treatment by administering erythropoietin and a physiologically tolerable iron preparation in amounts believed to be sufficient to bring the at least one parameter within the target range;

(ii) after the first administration in step (i), if the at least one parameter is determined to be less than the lower limit of the target range, conducting an additional treatment by administering the erythropoietin and iron preparation in amounts believed to be sufficient to bring the at least one parameter within the target range;

(iii) repeating step (ii) until the at least one parameter is determined to be within the target range and, once the at least one parameter reaches the target range, the amounts of erythropoietin and iron preparation used in the most recent repeat of step (ii) are considered optimal amounts; and thereafter (iv) conducting maintenance treatments in step (c) by administering the erythropoietin and iron preparation at the optimal amounts.

25. A pharmaceutical combination preparation suitable for the treatment of hemodialysis patients or patients exhibiting anemia, comprising about 2,000–7,000 U of erythropoietin and a physiologically tolerable iron preparation equivalent to about 1–20 mg or iron ions as a pharmaceutical formulation in a single container.

26. The pharmaceutical combination preparation of claim 25, comprising 5,000 U of erythropoietin and a physiologically tolerable iron preparation equivalent to 10 mg of iron ions.

27. The pharmaceutical combination preparation of claim 25, comprising about 2,000–4,000 U of erythropoietin and a physiologically tolerable iron preparation equivalent to about 3–10 mg of iron ions.

28. The pharmaceutical combination preparation of claim 25, comprising 3,000 U of erythropoietin and a physiologically tolerable iron preparation equivalent to 5 mg of iron ions.

29. The pharmaceutical combination preparation of claim 25, wherein the erythropoietin and iron preparation are packaged as a single pharmaceutical formulation in the form of an injection solution, infusion solution or lyophilizate.

30. The pharmaceutical combination preparation of claim 26, wherein the erythropoietin and iron preparation are packaged as a single pharmaceutical formulation in the form of an injection solution, infusion solution or lyophilizate.

31. The pharmaceutical combination preparation of claim 27, wherein the erythropoietin and iron preparation are packaged as a single pharmaceutical formulation in the form of an injection solution, infusion solution or lyophilizate.

32. The pharmaceutical combination preparation of claim 28, wherein the erythropoietin and iron preparation are packaged as a single pharmaceutical formulation in the form of an injection solution, infusion solution or lyophilizate.

33. A method for the production of a pharmaceutical combination preparation useful for the treatment of hemodialysis patients, comprising formulating about 2,000–7,000 U of erythropoietin and a physiologically tolerable iron preparation equivalent to about 1–20 mg or iron ions in a single pharmaceutical packing unit.

34. The method of claim 33 for the production of a pharmaceutical combination preparation useful for the treatment of patients exhibiting anemia, comprising formulating about 2,000–4,000 U of erythropoietin and a physiologically tolerable iron preparation equivalent to about 3–10 mg of iron ions in a pharmaceutical packing unit.

* * * * *